US009321992B2

(12) United States Patent
Dennis et al.

(10) Patent No.: US 9,321,992 B2
(45) Date of Patent: *Apr. 26, 2016

(54) CELL TARGETING METHODS AND COMPOSITIONS

(75) Inventors: James E. Dennis, Cleveland Heights, OH (US); Arnold I. Caplan, Cleveland Heights, OH (US); Nir Cohen, Tel Aviv (IL)

(73) Assignee: Case Western Reserve University, Cleveland, OH (US)

( * ) Notice: Subject to any disclaimer, the term of this patent is extended or adjusted under 35 U.S.C. 154(b) by 1933 days.

This patent is subject to a terminal disclaimer.

(21) Appl. No.: 10/461,887

(22) Filed: Jun. 13, 2003

(65) Prior Publication Data

US 2004/0048370 A1 Mar. 11, 2004

Related U.S. Application Data

(60) Provisional application No. 60/389,079, filed on Jun. 14, 2002.

(51) Int. Cl.
| | |
|---|---|
| *C12N 5/20* | (2006.01) |
| *A61K 35/12* | (2015.01) |
| *C12N 5/077* | (2010.01) |
| *C07K 16/18* | (2006.01) |
| *C12N 5/00* | (2006.01) |

(52) U.S. Cl.
CPC .............. *C12N 5/0655* (2013.01); *C07K 16/18* (2013.01); *C12N 5/0006* (2013.01); *A61K 35/12* (2013.01)

(58) Field of Classification Search
None
See application file for complete search history.

(56) References Cited

U.S. PATENT DOCUMENTS

| | | | |
|---|---|---|---|
| 5,486,359 A | | 1/1996 | Caplan et al. |
| 5,541,295 A | * | 7/1996 | Barrach et al. ............. 530/388.1 |
| 5,702,892 A | | 12/1997 | Mulligan-Kehoe |
| 5,736,396 A | | 4/1998 | Bruder et al. |
| 5,750,373 A | | 5/1998 | Garrard et al. |
| 5,821,047 A | | 10/1998 | Garrard et al. |
| 5,827,735 A | | 10/1998 | Young et al. |
| 5,843,780 A | | 12/1998 | Thomson |
| 5,906,934 A | | 5/1999 | Grande et al. |
| 5,948,635 A | | 9/1999 | Kay et al. |
| 6,127,132 A | | 10/2000 | Breitling et al. |
| 6,200,806 B1 | | 3/2001 | Thomson |
| 6,214,369 B1 | | 4/2001 | Grande et al. |
| 6,261,554 B1 | | 7/2001 | Valerio et al. |
| 6,316,256 B1 | * | 11/2001 | Tykocinski et al. ........... 435/325 |
| 6,835,377 B2 | * | 12/2004 | Goldberg ............. C12N 5/0655 424/93.7 |
| 7,282,222 B2 | * | 10/2007 | Phillips ........................ 424/577 |
| 2002/0110544 A1 | * | 8/2002 | Goldberg ............. C12N 5/0655 424/93.7 |
| 2003/0149235 A1 | | 8/2003 | Baker et al. |
| 2006/0034767 A1 | | 2/2006 | Lum et al. |
| 2009/0274712 A1 | * | 11/2009 | Dennis ............. A61K 47/48776 424/178.1 |

FOREIGN PATENT DOCUMENTS

| | | |
|---|---|---|
| WO | WO 98/53804 | 12/1998 |
| WO | WO 99/46284 | 9/1999 |
| WO | WO 00/02654 A1 | 1/2000 |
| WO | WO 00/23570 | 4/2000 |
| WO | WO 00/53795 A1 | 9/2000 |
| WO | WO 01/11011 A3 | 2/2001 |
| WO | WO 01/92549 A2 | 12/2001 |
| WO | WO 02/02751 | 1/2002 |
| WO | WO 02/20722 A2 | 3/2002 |
| WO | WO 02/090985 A1 | 11/2002 |
| WO | WO 03/009881 A2 | 2/2003 |
| WO | WO 03/072542 A2 | 9/2003 |
| WO | WO 03/106640 | 12/2003 |

OTHER PUBLICATIONS

Osiris Therapeutics, Inc. Osiris Announces Top-Line Interm Results for Stem Cell Trial for Knee Repair. Feb. 12, 2007. pp. 1-2.*
Takagi and Jasin. Interactions of synovial fluid immunoglobulins with chondrocytes. Arthritis and Rheumatism 35(12):1502-1509, 1992.*
Takagi and Jasin. Interactions between anticollagen antibodies and chondrocytes. Arthritis and Rheumatism 35(2):224230, 1992.*
Owens RJ, Young RJ. The genetic engineering of monoclonal antibodies. J Immunol Methods. 168(2):149-165, 1994.*
Nixon, AJ.; Fortier, LA. New horizons in articular cartilage repair. AAEP. 2001. pp. 217-226.*
Nehrer et al. Canine chondrocytes seeded in type I and type II collagen implants investigated in vitro. J Biomed Mater Res. 1997 Summer;38(2):95-104.*
Caplan, Arnold I. and Bruder, Scott P. "Mesenchymal Stem Cells: Building Blocks for Molecular Medicine in the 21st Century", Trends in Molecular Medicine, vol. 7, No. 6, Jun. 2001, pp. 259-264.
Buckwalter, et al. Changes in Proteoglycan Aggregates During Cartilage Mineralization. Calcif Tissue Int., 41:228-36 (1987).
Lippiello, et al. Collagen Synthesis in Normal and Osteoarthritic Human Cartilage. J Clin Invest., 59:593-600 (1977).
Eyre, et al. Biosynthesis of Collagen and other Matrix Proteins by Articular Cartilage in Experimental Osteoarthrosis. Biochem J., 188:823-37 (1980).
Owen. Marrow stromal stem cells. J. Cell Sci Suppl., 10:63-76 (1988).
Caplan, et al. Principles of Cartilage Repair and Regeneration. Clin Orthop. 342:254-69 (1997).
Nakahara, et al. In Vivo Osteochondrogenic Potential of Cultured Cells Derived From the Periosteum. Clin Orthop., 259:223-32 (1990).
Brittberg. Autologous Chondrocyte Transplantation. Clin Orthop., 367 Suppl.:S147-55 (1999).
Maniwa, et al. Effects of hyaluronic acid and basic fibroblast growth factor on motility of chondrocyts and synovial cells in culture. Acta Orthop Scand., 72:299-303 (2001).

(Continued)

*Primary Examiner* — Maher Haddad
(74) *Attorney, Agent, or Firm* — Tarolli, Sundheim, Covell & Tummino LLP

(57) ABSTRACT

In certain aspects, the invention relates to cell delivery compositions comprising a chondrogenic cell and a targeting moiety. Such compositions may be used, for example, in administering a targeted cell therapy to a subject.

17 Claims, 8 Drawing Sheets

(56) References Cited

OTHER PUBLICATIONS

Convery, et al. Chondral Defects of the Knee. Contemp. Orthop., 28(2):100-7 (1994).
Blevins, et al. Treatment of Articular Cartilage Defects in Athletes: An Analysis of Functional Outcome and Lesion Appearance. Orthopedics, 21(7):761-7 (1998).
Sledge. Microfracture Techniques in the Treatment of Osteochondral Injuries. Clin Sports Med., 20(2):365-77 (2001).
Meyers, et al. Resurfacing of the Knee with Fresh Osteochondral Allograft. J Bone Joint Surg Am., 71A(5):704-13 (1989).
Buckwalter, et al. Restoration of Injured or Degenerated Articular Cartilage. J Am Acad Orthop Surg. 2:192-201 (1994).
Caplan. Tissue Engineering Designs for the Future: New Logics, Old Molecules. Tissue Eng., 6:1-8 (2000).
Itay, et al. Use of Cultured Embryonal Chick Epiphyseal Chondrocytes as Grafts for Defects in Chick Articular Cartilage. Clin Orthop., 220:284-303 (1987).
Brun, et al. Chondrocyte aggregation and reorganization into three-dimensional scaffolds. J Biomed Mater Res., 46:337-46 (1999).
Ochi, et al. Current Concepts in Tissue Engineering Technique for Repair of Cartilage Defect. Artif Organs., 25:172-9 (2001).
Brittberg, et al. Treatment of Deep Cartilage Defects in the Knee with Autologous Chondrocyte Transplantation. N Engl J Med., 331:889-95 (1994).
Hasler, et al. Articular Cartilage Biomechanics: Theoretical Models, Material Properties, and Biosynthetic Response. Crit Rev Biomed Eng., 27:415-88 (1999).
Heinegard, et al. Distribution of Keratan Sulfate in Cartilage Proteoglycans. J Biol Chem., 252:1971-9 (1977).
Sorrell, et al. Structural Domains in Chondroitin Sulfate Identified by Anti-Chondroitin Sulfate Monoclonal Antibodies. Immunosequencing of Chondroitin Sulfates. Matrix, 13:351-61 (1993).
Wakitani, et al. Repair of Large Full-Thickness Articular Cartilage Defects with Allograft Articular Chondrocytes Embedded in a Collagen Gel. Tissue Eng., 4:429-44 (1998).
Lennon, et al. A Chemically Defined Medium Supports in Vitro Proliferation and Maintains the Osteochondral Potential of Rat Marrow-Derived Mesenchymal Stem Cells. Exp Cell Res., 219:211-22 (1995).
Kim, et al. The use of palmitate-conjugated protein A for coating cells with artificial receptors which facilitate intercellular interactions. J Immunol Methods, 158:57-65 (1993).
Naumann, et al. Immunochemical and Mechanical Characterization of Cartilage Subtypes in Rabbit. J Histochem Cytochem., 50:1049-58 (2002).
O'Driscoll. Articular Cartilage Regeneration Using Periosteum. Clin Orthop., 367 Suppl.:S186-203 (1999).
Hangody, et al. Mosaicplasty for the Treatment of Osteochondritis Dissecans of the Talus: Two to Seven Year Results in 36 Patients. Foot Ankle Int., 22:552-8 (2001).
Jones, P., et al. Replacing the complementarity-determining regions in a human antibody with those from a mouse. Nature, 321:522-525 (1986).
Tempest, et al. Reshaping a Human Monoclonal Antibody to Inhibit Human Respiratory Syncytial Virus Infection in Vivo. Biotechnology, 9:266-273 (1991).
Skerra. Engineered protein scaffolds for molecular recognition. J Molecular Recognition, 13:167-187 (2000).
Colsky and Peacock. Palmitate-derivatized antibodies can function as surrogate receptors for mediating specific cell-cell interactions. J Immunol Methods, 124:179-87 (1989).
Bjorck, L. and Kronvall, G. Purification and Some Properties of Streptococcal Protein G, A Novel IgG-Binding Reagent. J. Immunol., 133(2):969-974 (1984).
Boyle, et al. Interaction of Bacterial Fc Receptors with Goat Immunoglobulins. Mol. Immunol. 22(9):1115-21 (1985).
Madry, et al. Overexpression of human insulin-like growth factor-I promotes new tissue formation in an ex vivo model of articular chondrocyte transplantation. Gene Therapy, 8(19):1443-1449 (2001).
Noth, et al. In Vitro Engineered Cartilage Constructs Produced by Press-Coating Biodegradable Polymer with Human Mesenchymal Stem Cells. Tissue Engineering 8(1):131-144 (2002).
Rombouts, et al. Primary murine MSC show highly efficient homing to the bone marrow but lose homing ability following culture. Leukemia, 17(1):160-170.
Akerman et al., "Nanocrystal targeting in vivo", PNAS, Oct. 1, 2002, vol. 99, No. 20, pp. 12617-12621.
Gerstenfeld, et al., "Chondrocytes provide morphogenic signals that selectively induce osteogenic differentiation of mesenchymal stem cells", J Bone Miner Res. Feb. 2002;17(2):221-30, Abstract only.
Trepel et al., "Molecular adaptors for vascular-targeted adenoviral gene delivery", Human Gene Ther. Sep. 20, 2000;11(14):1971-81, Abstract only.
Samoylova et al., "Targeting peptides for microglia identified via phage display", Journal of Neuroimmunology, vol. 127, Issues 1-2, Jun. 2002, pp. 13-21, Abstract only.
Thomas, et al., "Cartilage collagens: strategies for the study of their organization and expression in the extracellular matrix", Annals of the Rheumatic Diseases 1994; 53:488-496.
Chen et al., "Hierarchial costimulator thresholds for distinct immune responses: application of a novel two-step Fc fusion protein transfer method", *The Journal of Immunology*, 2000, 164: 705-711.
Darling, D., et al., "In Vitro immune modulation by antibodies coupled to tumour cells", Gene Therapy (1997) 4, No. 12, 1350-1360.
Dennis, James E., et al., "Targeted delivery of progenitor cells for cartilage repair", Journal of Orthopaedic Research 22 (2004) 735-741.
Yoo, J.U., et al., "The Chondrogenic Potential of Human Bine-Marrow-Derived Mesenchymal Progenitor Cells", *The Journal of Bone and Joint Surgery, Incorporated*, vol. 80-A, No. 12, 1998, pp. 1745-1757.

* cited by examiner

CELL TARGETING METHODS AND COMPOSITIONS

CROSS-REFERENCE TO RELATED APPLICATIONS

This application claims the benefit of priority of U.S. Provisional Application No. 60/389,079 filed Jun. 14, 2002, the specification of which is incorporated by reference herein in its entirety.

FUNDING

Work described herein was supported by National Institutes of Health Grant 1RO1AR 48316-01. The United States Government has certain rights in the invention.

BACKGROUND

Articular cartilage is a distinct tissue because it is aneural, avascular, and has a very limited capability for self-repair (Buckwalter et al., 1987, Calcif Tissue Int., 41:228-36; Hunziker et al., 1996, J Bone Joint Surg Am., 78:721-33). Traumatic and mechanical injuries, whether full or partial thickness, cannot spontaneously heal and degeneration usually prevails over regeneration and osteoarthritis develops. On the molecular level, osteoarthritis develops as a consequence of the sequential destruction of the articular cartilage surface, which includes the release of cartilage matrix molecules, such as collagens and aggrecan from the articular surface (Dodge et al., 1989, J Clin Invest., 83:647-61; Sandy et al., 1984, Arthritis Rheum., 27:388-97). Although damaged cartilage has a very limited self-repair capability there is evidence that remaining articular chondrocytes do attempt to compensate for matrix degradation by up-regulating matrix molecules production (Lippiello et al., 1977, J Clin Invest., 59:593-600; Eyre et al., 1980, Biochem J., 188:823-37). Ultimately, this up-regulation in chondrocyte metabolic activity and cartilage matrix production is insufficient to compensate for the catabolic events and the continued destruction of cartilage is exacerbated by the limited ability of adult chondrocytes to divide and replace lost chondrocytes. One of the major reasons for this "losing battle" is the fact that cartilage as a non-vascularized tissue, does not have access to a source of stem cells, such as the mesenchymal stem cells of bone marrow (Owen, 1988, J Cell Sci Suppl., 10:63-76; Caplan et al., 1997, Clin Orthop., 342:254-69), nor does articular cartilage have a source of pre-chondrogenic cells, as is found in the periosteum (Nakahara et al., 1990, Clin Orthop., 259:223-32; O'Driscoll, 1999, Clin Orthop., 367 Suppl:S186-203; Brittberg, 1999, Clin Orthop., 367 Suppl:S147-55). Short of completely replacing the articular cartilage, methods directed at the repair of cartilage must overcome these inherent self-repair deficiencies either by promoting increased chondrogenesis of cells within the articular cartilage or by increasing the number of chondrogenic cells at the injured area. Therapies directed to treat damaged cartilage are very limited and are divided into two general approaches. The first approach is non-surgical treatments such as analgesics, non-steroidal anti inflammatory drugs, and even localized intraarticular injections of steroids. This treatment option is often combined with modification of weight bearing and physical therapy aimed at pain relief, muscle strengthening, and the preservation of range of motion. All the above-mentioned are aimed at pain relief and none have been shown to affect the natural disease progression or the cause of the problem. Another non surgical technique used to enhance healing, is the local application of growth factors and oral supplements such as TGF-B, hyaluronic acid and chondroitin sulphate in an effort to change the environment so it will be favorable for healing (Maniwa et al., 2001, Acta Orthop Scand., 72:299-303). The second general approach is surgical and it is divided into three main categories: treatments that aim at promoting self-healing doing that by changing the local environment by allowing cells originating in adjacent tissue (bone marrow) to migrate, adhere, multiply and repair the injured site. This is done by penetrating the sub-chondral bone, for example, the arthroscopic shaving technique, sub-chondral drilling and sub-chondral micro-fractures (Convery et al., 1994, Contemp Orthop., 28:101-7; Blevins et al., 1998, Orthopedics., 21:761-7; Sledge, 2001, Clin Sports Med., 20:365-77). Other surgical treatments include osteochondral grafting, either allogeneic or autogeneic, in an effort to reconstruct the defect area (Meyers et al., 1989, J Bone Joint Surg Am., 71:704-13; Buckwalter et al., 1994, J Am Acad Orthop Surg.m 2:192-201; Hangody et al., 2001, Foot Ankle Int., 22:552-8) by using healthy osteochondral implants. The third surgical approach is based on tissue engineering, the end goal of which is regenerative fabrication of tissues by manipulating cells, scaffolds and signals in-vitro (Caplan, 2000, Tissue Eng., 6:1-8). Current applications of tissue engineering to articular cartilage have focused on manipulating cartilage-forming cells, committed chondrocytes (Itay et al., 1987, Clin Orthop., 220:284-303) or osteochondral progenitor cells (Yoo et al., 1998, J Bone Joint Surg Am., 80:1745-57) as a source for the tissue regenerated. One of the cornerstones/obstacles in implementing this technology is being able to direct the cells or tissue, engineered in vitro, to the precise in vivo site were repair is needed. Research focused on numerous delivery vehicles onto which the cells are loaded is taking place worldwide (Brun et al., 1999, J Biomed Mater Res., 46:337-46; Ochi et al., 2001, Artif Organs., 25:172-9) and techniques in which cells are injected into surgically constructed pockets have been published (Brittberg et al., 1994, N Engl J. Med., 331:889-95).

Efforts in tissue engineering and restorative surgery would be improved by advances in cell targeting technology.

SUMMARY

This application provides compositions and methods for targeting cells to a specific site, such as a site of injury or a site of cartilage or bone defect. In one aspect, the application provides a cell delivery composition comprising cells linked to a targeting moiety, wherein the targeting moiety is selected so that it interacts with selected tissue at the site of injury, such selected tissue may be cartilage, for example, articular cartilage. In one embodiment, the application provides a cell delivery composition that targets chondrogenic cells to the cartilage matrix using a targeting moiety that interacts with the cartilage matrix.

The targeting moieties that are useful in these compositions include a component of a specific binding pair. In certain delivery compositions, the targeting moiety may be an antibody, such as a monoclonal or polyclonal antibody. In other embodiments, the targeting moiety may be selected from the group consisting of an Fv fragment, single chain Fv (scFv) fragment, Fab' fragment, F(ab')2 fragment, single domain antibody, camelized antibody, humanized antibody, diabodies, tribodies, tetrabodies.

In yet other embodiments the antibody maybe modified with a hydrophobic moiety, such as a palmitoyl moiety or myristoyl moiety. In a preferred embodiment, the antibody interacts with cartilage matrix and may be selected from the following group: anti-collagen type II, anti-chondroitin 4-sulfate and anti-keratan sulfate.

In yet another aspect, the targeting moiety may be a receptor, a ligand, or an aptamer.

The cells such as the chondrogenic cells may be linked to the targeting moiety either directly or indirectly via a linker. Examples of such linkers include protein G and protein A.

In certain embodiments, the invention relates to a polypeptide composition comprising a protein G polypeptide covalently, or optionally non-covalent but stably, associated with a lipophilic moiety.

The embodiments and practices of the present invention, other embodiments, and their features and characteristics, will be apparent from the description, figures and claims that follow, with all of the claims hereby being incorporated by this reference into this Summary.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION

Figure 1:
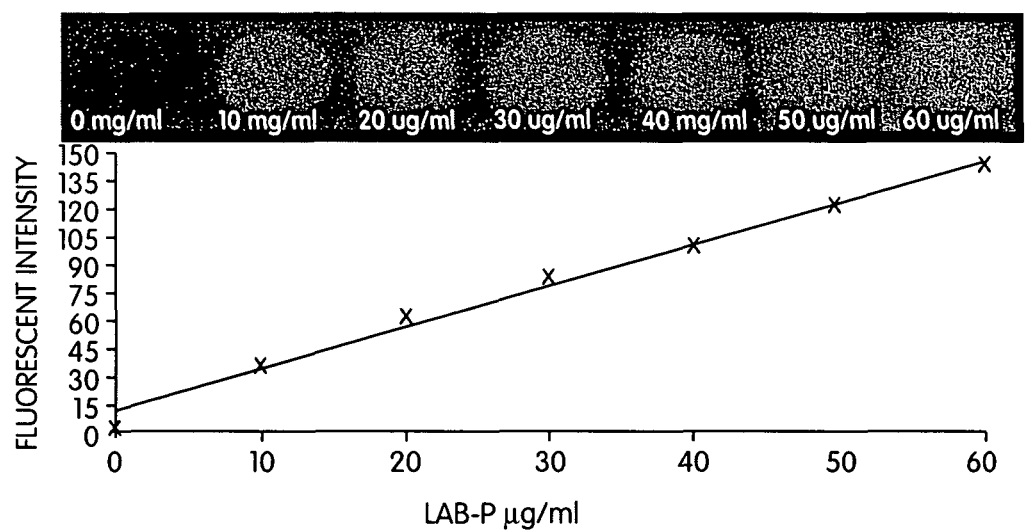
FIG. 1. The graph shows the concentration of palmitated protein G (PPG) (or lipidated antibody binding protein, LAB-P) on the x-axis, and the relative fluorescence intensity in arbitrary units on the y-axis. The insert shows fluorescent micrographs of representative cells coated with PPG.

Definitions:

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. In exemplary embodiments, antibodies used with the methods and compositions described herein are derivatives of the IgG class.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "chondrogenic cells" includes chondrocytes and cells that differentiate into chondrocytes. The term may also refer to cells that are genetically altered or otherwise manipulated so as to become cells that produce substantial components of the cartilage matrix.

The term "diabodies" refers to dimeric scFvs. The components of diabodies typically have shorter peptide linkers than most scFvs and they show a preference for associating as dimers.

As used herein, the term "epitope" refers to a physical structure on a molecule that interacts with a selective component. In exemplary embodiments, epitope refers to a desired region on a target molecule that specifically interacts with a selectivity component.

The term "Fab" refers to an antibody fragment that is essentially equivalent to that obtained by digestion of immunoglobulin (typically IgG) with the enzyme papain. The heavy chain segment of the Fab fragment is the Fd piece. Such fragments may be enzymatically or chemically produced by fragmentation of an intact antibody, recombinantly produced from a gene encoding the partial antibody sequence, or it may be wholly or partially synthetically produced.

The term "Fab'" refers to an antibody fragment that is essentially equivalent to that obtained by reduction of the disulfide bridge or bridges joining the two heavy chain pieces in the $F(ab')_2$ fragment. Such fragments may be enzymatically or chemically produced by fragmentation of an intact antibody, recombinantly produced from a gene encoding the partial antibody sequence, or it may be wholly or partially synthetically produced.

The term "$F(ab')_2$" refers to an antibody fragment that is essentially equivalent to a fragment obtained by digestion of an immunoglobulin (typically IgG) with the enzyme pepsin at pH 4.0-4.5. Such fragments may be enzymatically or chemically produced by fragmentation of an intact antibody, recombinantly produced from a gene encoding the partial antibody sequence, or it may be wholly or partially synthetically produced.

The term "Fv" refers to an antibody fragment that consists of one $V_H$ and one $V_L$ domain held together by noncovalent interactions. The term "dsFv" is used herein to refer to an Fv with an engineered intermolecular disulfide bond to stabilize the $V_H$-$V_L$ pair.

The term "immunogen" traditionally refers to compounds that are used to elicit an immune response in an animal, and is used as such herein. However, many techniques used to produce a desired selectivity component, such as the phage display and aptamer methods described below, do not rely wholly, or even in part, on animal immunizations. Nevertheless, these methods use compounds containing an "epitope," as defined above, to select for and clonally expand a population of selectivity components specific to the "epitope." These in vitro methods mimic the selection and clonal expansion of immune cells in vivo, and, therefore, the compounds containing the "epitope" that is used to clonally expand a desired population of phage, aptamers and the like in vitro are embraced within the definition of "immunogens."

The terms "single-chain Fvs" and "scFvs" refers to recombinant antibody fragments consisting of only the variable light chain ($V_L$) and variable heavy chain ($V_H$) covalently connected to one another by a polypeptide linker. Either $V_L$ or $V_H$ may be the $NH_2$-terminal domain. The polypeptide linker may be of variable length and composition so long as the two variable domains are bridged without serious steric interference. In exemplary embodiments, the linkers are comprised primarily of stretches of glycine and serine residues with some glutamic acid or lysine residues interspersed for solubility.

As used herein, the term "targeting moiety" refers to a moiety capable of interacting with a target molecule. Targeting moieties having limited cross-reactivity are generally preferred. In certain embodiments, suitable targeting moieties include, for example, any member of a specific binding pair, antibodies, monoclonal antibodies, or derivatives or analogs thereof, including without limitation: Fv fragments, single chain Fv (scFv) fragments, Fab' fragments, $F(ab')_2$ fragments, single domain antibodies, camelized antibodies and antibody fragments, humanized antibodies and antibody fragments, and multivalent versions of the foregoing; multivalent binding reagents including without limitation: monospecific or bispecific antibodies, such as disulfide stabilized Fv fragments, scFv tandems (($scFv)_2$ fragments), diabodies, tribodies or tetrabodies, which typically are covalently linked or otherwise stabilized (i.e., leucine zipper or helix stabilized) scFv fragments; and other targeting moieties include for example, aptamers, receptors, ligands, and fusion proteins.

Overview:

In certain embodiments, the approach described herein is based on a cell coating technique that generates delivery compositions comprising a cell and a targeting moiety, where the targeting moiety is designed to bind to a target location, such as a tissue, extracellular matrix, cell type, etc. In certain embodiments the cell is a chondrogenic cell and the targeting moiety binds cartilage matrix. The cell coating technique enhances adherence of chondrogenic cells, such as osteochondral progenitor cells, to cartilage matrix injury site by coating the cells with matrix specific antibodies. We show that this enhanced adherence of cells increases the number of chondrogenic cells at the articular injury site, and, while not wishing to be bound to theory, it is expected that, the increased presence of cells at the injury site shifts the balance of the repair process into a net anabolic one.

In certain embodiments, the cell coating technique employs a linker to connect the cell to the targeting moiety. For example, protein A and protein G are useful linkers where the targeting moiety comprises an antibody. In certain embodiments, the linker is connected to the cell by a lipophilic moiety, as in the case of palmitated protein A or protein G. The lipophilic moiety of the palmitate hydrocarbon chains makes it possible to coat the cell membrane with this linker by insertion into the outer leaflet of the phospholipid bilayer.

Cells

Methods described herein may employ any cell that is suitable for the targeted tissue, matrix, etc. In certain embodiments, the cells are chondrogenic cells. Exemplary chondrogenic cells include chondrocytes such as articular chondrocytes. In certain embodiments, chondrocytes may be identified by propidium iodide staining, where chondrocytes are surrounded by meta-chromatic staining representing highly sulfated glycosaminoglycans. Chondrogenic cells also include cells that can differentiate or give rise to chondrocytes. Exemplary cells that differentiate to form chondrocytes or give rise to chondrocytes include mesenchymal stem cells, stem cells derived from adipose tissue, osteochondral progenitor cells; embryonic stem cells; multipotent adult stem cells, etc. Exemplary cells and methods for obtaining such cells are described in the following U.S. patents (prefaced by "US") and international patent applications (prefaced by "WO"): U.S. Pat. Nos. 5,486,359; 5,736,396; 6,214,369; 5,906,934; 5,827,735; 6,200,806; 5,843,780; WO 00/53795; WO 00/02654; WO 01/11011.

In certain embodiments, the cells are immunologically matched to the subject who will receive them (e.g., similar HLA typing), and optionally, the cells are autologous, meaning that they are derived from the subject.

Targeting Moieties, Linkers and Lipophilic Moieties

A targeting moiety may be any molecule, or complex of molecules, which is capable of interacting with a desired target, including, for example, a tissue, a cell type, an extracellular matrix, a carbohydrates, a protein, etc. Exemplary targeting moieties may include, for example, antibodies, antibody fragments, non-antibody receptor molecules, aptamers, etc. A targeting moiety may include additional components that assist in forming an attachment between the targeting moiety and a coated cell. Targeting moieties having limited cross-reactivity are generally preferred.

In certain embodiments, the strategies used to target cells to cartilage are based on the composition and structure of the primary extracellular matrix molecules contained in cartilage. Any available antigen in cartilage may be used as a target for a targeting moiety. A primary target for promoting chondrocyte cell attachment is type II collagen, which is the most abundant fibrillar collagen in cartilage. The next most prominent molecules, based on dry weight, are the proteoglycans, which represent 20-30% of the cartilage dry weight (Hasler et al., 1999, Crit Rev Biomed Eng., 27:415-88). Although abundant, collagen type II fibers are masked by other molecules, especially proteoglycan molecules that are often observed to be in direct contact with the collagen fibers. As a percentage of volume proteoglycans are much more abundant then collagen type II and in addition, it is known from structural and biochemical analysis of proteoglycans (Heinegard et al., 1977, J Biol Chem., 252:1971-9) that there are hundreds of chondroitin sulfate and keratan sulfate side chains on each aggrecan molecule, and since each glycosaminoglycan side chain can have multiple antigenic epitopes, proteoglycans are key targets for these cell-binding strategies. A previous study from this laboratory documents the accessibility of chondroitin and keratan-sulfate chains to antibody binding before and after moderate chondroitinase ABC digestion (Sorrell et al., 1993, Matrix., 13:351-61). Based on this data, a set of antibodies were selected that are most likely to bind to cartilage matrix. The antibodies that answer these criteria were; anti type II collagen (11-116B3), anti keratan sulphate (5D4), and anti chondroitin-4-sulfate (2B6) and a combination of the different antibodies.

In certain embodiments, the targeting moiety may be an antibody or an antibody fragment. For example, targeting moieties may be monoclonal antibodies, or derivatives or analogs thereof, including without limitation: Fv fragments, single chain Fv (scFv) fragments, Fab' fragments, F(ab')$_2$ fragments, single domain antibodies, camelized antibodies and antibody fragments, humanized antibodies and antibody fragments, and multivalent versions of the foregoing; multivalent targeting moieties including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; receptor molecules which naturally interact with a desired target molecule.

Preparation of antibodies may be accomplished by any number of well-known methods for generating monoclonal antibodies. These methods typically include the step of immunization of animals, typically mice, with a desired immunogen (e.g., a desired target molecule or fragment thereof). Once the mice have been immunized, and preferably boosted one or more times with the desired immunogen(s), monoclonal antibody-producing hybridomas may be prepared and screened according to well known methods (see, for example, Kuby, Janis, *Immunology*, Third Edition, pp. 131-139, W. H. Freeman & Co. (1997), for a general overview of monoclonal antibody production, that portion of which is incorporated herein by reference).

Over the past several decades, antibody production has become extremely robust. In vitro methods that combine antibody recognition and phage display techniques allow one to amplify and select antibodies with very specific binding capabilities. See, for example, Holt, L. J. et al., "The Use of Recombinant Antibodies in Proteomics," *Current Opinion in Biotechnology* 2000, 11:445-449, incorporated herein by reference. These methods typically are much less cumbersome than preparation of hybridomas by traditional monoclonal antibody preparation methods. Binding epitopes may range in size from small organic compounds such as bromo uridine and phosphotyrosine to oligopeptides on the order of 7-9 amino acids in length.

In one embodiment, phage display technology may be used to generate a targeting moiety specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding an scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as an Fab' fragment, may be cloned into phage display vectors for surface expression on phage particles. The phage may be any phage, such as lambda, but typically is a filamentous phage, such as fd and M13, typically M13.

In phage display vectors, the $V_H$-linker-$V_L$ sequence is cloned into a phage surface protein (for M13, the surface proteins g3p (pIII) or g8p, most typically g3p). Phage display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacteria cells is the Recombinant Phage Antibody System (RPAS), commercially available from Amersham Pharmacia Biotech, Inc. of Piscataway, N.J. and the pSKAN Phagemid Display System, commercially available from MoBiTec, LLC of Marco Island, Fla. Phage display systems, their construction and screening methods are described in detail in, among others, U.S. Pat. Nos. 5,702, 892, 5,750,373, 5,821,047 and 6,127,132, each of which are incorporated herein by reference in their entirety.

A targeting moiety need not originate from a biological source. A targeting moiety may, for example, be screened from a combinatorial library of synthetic peptides. One such method is described in U.S. Pat. No. 5,948,635, incorporated herein by reference, which described the production of phagemid libraries having random amino acid insertions in the pIII gene of M13. These phage may be clonally amplified by affinity selection as described above.

The immunogens used to prepare targeting moieties having a desired specificity will generally be the target molecule, or a fragment or derivative thereof. Such immunogens may be isolated from a source where they are naturally occurring or may be synthesized using methods known in the art. For example, peptide chains may be synthesized by 1-ethyl-3-[dimethylaminopropyl] carbodiimide (EDC)-catalyzed condensation of amine and carboxyl groups. It certain embodiments, the immunogen may be linked to a carrier bead or protein. For example, the carrier may be a functionalized bead such as SASRIN™ resin commercially available from Bachem, King of Prussia, Pa. or a protein such as keyhole limpet hemocyanin (KLH) or bovine serum albumin (BSA). The immunogen may be attached directly to the carrier or may be associated with the carrier via a linker, such as a non-immunogenic synthetic linker (for example, a polyethylene glycol (PEG) residue, amino caproic acid or derivatives thereof) or a random, or semi-random polypeptide.

In certain embodiments, it may be desirable to mutate the binding region of a polypeptide targeting moiety and select for a targeting moiety with superior binding characteristics as compared to the un-mutated targeting moiety. This may be accomplished by any standard mutagenesis technique, such as by PCR with Taq polymerase under conditions that cause errors. In such a case, the PCR primers could be used to amplify scFv-encoding sequences of phagemid plasmids under conditions that would cause mutations. The PCR product may then be cloned into a phagemid vector and screened for the desired specificity, as described above.

In other embodiments, the targeting moieties may be modified to make them more resistant to cleavage by proteases. For example, the stability of targeting moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of targeting moiety may be of the D configuration. The switch from L to D amino acids neutralizes the digestion capabilities of many of the ubiquitous peptidases found in the digestive tract. Alternatively, enhanced stability of a targeting moiety comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of a targeting moiety may be achieved by intercalating one or more dextrorotatory amino acids (such as, dextrorotatory phenylalanine or dextrorotatory tryptophan) between the amino acids of targeting moiety. In exemplary embodiments, such modifications increase the protease resistance of a targeting moiety without affecting the activity or specificity of the interaction with a desired target molecule.

In certain embodiments, the antibodies or variants thereof, may be modified to make them less immunogenic when administered to a subject. For example, if the subject is human, the antibody may be "humanized"; where the complimentarity determining region(s) of the hybridoma-derived antibody has been transplanted into a human monoclonal antibody, for example as described in Jones, P. et al. (1986), Nature 321, 522-525 or Tempest et al. (1991) Biotechnology 9, 266-273. Also, transgenic mice, or other mammals, may be used to express humanized antibodies. Such humanization may be partial or complete.

In other embodiments, the targeting moiety may comprise a non-antibody receptor molecule, including, for example, receptors which naturally recognize a desired target molecule, receptors which have been modified to increase their specificity of interaction with a target molecule, receptor molecules which have been modified to interact with a desired target molecule not naturally recognized by the receptor, and fragments of such receptor molecules (see, e.g., Skerra, J. Molecular Recognition 13: 167-187 (2000)).

In still other embodiments, the targeting moiety may comprise an aptamer. Aptamers are oligonucleotides that are selected to bind specifically to a desired molecular structure. Aptamers typically are the products of an affinity selection process similar to the affinity selection of phage display (also known as in vitro molecular evolution). The process involves performing several tandem iterations of affinity separation, e.g., using a solid support to which the desired immunogen is bound, followed by polymerase chain reaction (PCR) to amplify nucleic acids that bound to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof, such as, without limitation, peptide nucleic acids (PNAs) and phosphorothioate nucleic acids.

In certain embodiments, a targeting moiety of the invention may contain a tag which facilitates its isolation, immobilization, identification, or detection and/or which increases its solubility. Exemplary tags, include, for example, glutathione S-transferase (GST), calmodulin-binding peptide, thioredoxin, maltose binding protein, HA, myc, poly arginine, poly His, poly His-Asp or FLAG tags. Additional exemplary tags include polypeptides that alter protein localization in vivo, such as signal peptides, type III secretion system-targeting peptides, transcytosis domains, nuclear localization signals, etc. In various embodiments, a targeting moiety of the invention may comprise one or more tags, including multiple copies of the same tag or two or more different tags. It is also within the scope of the invention to include a spacer (such as a polypeptide sequence or a chemical moiety) between a targeting moiety of the invention and the tag in order to facilitate construction or to optimize its structural constraints. In another embodiment, the tagged moiety may be constructed so as to contain protease cleavage sites between the tag and the moiety in order to remove the tag. Examples of suitable endoproteases for removal of a tag, include, for example, Factor Xa and TEV proteases.

A targeting moiety may be directly associated with a cell. This may be achieved, for example, by modifying the targeting moiety with a lipophilic moiety to allow insertion into or association with the cell membrane. Methods for inserting a palmitated antibody into a cell membrane are described, for example, in Colsky and Peacock, J Immunol Methods 1989 124:179-87. Direct attachment to a cell may also be achieved by covalently attaching the targeting moiety to another element that has an affinity for a marker on the surface of the cell to be coated, such as an extracellular protein or oligosaccharide. Indirect attachment may achieved, for example, by providing a linker that associates with the cell to be coated and with the targeting moiety. Exemplary linkers include Protein G. Protein G is a highly stable surface receptor from Streptococcus sp. (Lancefield Group G), that has four Fc-fragment binding sites for immunoglobulins and each molecule can bind 2 molecules of IgG (Bjorck L and G. 1984; Boyle and Reis 1987). Another exemplary linker is Protein A, which also binds Fc fragments, but with a different range of specificities. Linkers may be modified to associate with a cell through any of the various approaches described above with respect to direct attachment of a targeting moiety. For example, the linker may be modified with a lipophilic moiety. In certain exemplary embodiment, the linker is palmitated protein G or palmitated protein A.

In certain embodiments, linkers or targeting moieties may be attached to a cell by covalent linkage to a lipophilic moiety that inserts into or associates with a cell membrane. There are a wide range of lipophilic moieties with which linkers or targeting moieties may be derivatived. A lipophilic group can be, for example, a relatively long chain alkyl or cycloalkyl (preferably n-alkyl) group having approximately 7 to 30 carbons. The alkyl group may terminate with a hydroxy or primary amine "tail". To further illustrate, lipophilic molecules include alicyclic hydrocarbons, saturated and unsaturated fatty acids and other lipid and phospholipid moieties, waxes, cholesterol, isoprenoids, terpenes and polyalicyclic hydrocarbons including adamantane and buckminsterfullerenes, vitamins, polyethylene glycol or oligoethylene glycol, (C1-C18)-alkyl phosphate diesters, —O—CH2-CH(OH)—O—(C12-C18)-alkyl, conjugates with pyrene derivatives, esters and alcohols, other lipid molecules, cage structures such as adamantane and buckminsterfullerenes, and aromatic hydrocarbons such as benzene, perylene, phenanthrene, anthracene, naphthalene, pyrene, chrysene, and naphthacene. The lipophilic moiety can be a lipophilic dye suitable for use in the invention include, but are not limited to, diphenylhexatriene, Nile Red, N-phenyl-1-naphthylamine, Prodan, Laurodan, Pyrene, Perylene, rhodamine, rhodamine B, tetramethylrhodamine, Texas Red, sulforhodamine, 1,1'-didodecyl-3,3,3',3'tetramethylindocarbocyanine perchlorate, octadecyl rhodamine B and the BODIPY dyes available from Molecular Probes Inc. Other exemplary lipophilic moieties include aliphatic carbonyl radical groups such as decanoyl, dodecanoyl, dodecenoyl, tetradecadienoyl, decynoyl or dodecynoyl.

The N-terminal amine of a protein can be modified preferentially relative to other amines in a protein because its lower pKa results in higher amounts of the reactive unprotonated form at neutral or acidic pH. Aryl halides, aldehydes and ketones, acid anhydrides, isocyanates, isothiocyanates, imidoesters, acid halides, N-hydroxysuccinimidyl (e.g., sulfo-NHS-acetate), nitrophenyl esters, acylimidazoles, and other activated esters and thioesters are among those known to react with amine functions.

There are a variety of chemical methods for the modification of many amino acid side chains, such as cysteine, lysine, histidine, aspartic acid, glutamic acid, serine, threonine, tyrosine, arginine, methionine, and tryptophan. Therefore a lipophilic moiety may be attached to an amino acid other than at the N-terminus.

To illustrate, there are a large number of chemical cross-linking agents that are known to those skilled in the art. Heterobifunctional cross-linkers provide the ability to design more specific coupling methods for conjugating to proteins, thereby reducing the occurrences of unwanted side reactions such as homo-protein polymers. A wide variety of heterobifunctional cross-linkers are known in the art. These include succinimidyl 4-(N-maleimidomethyl) cyclohexane-1-carboxylate (SMCC), m-Maleimidobenzoyl-N— hydroxysuccinimide ester (MBS); N-succinimidyl (4-iodoacetyl) aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl-a-methyl-a-(2-pyridyldithio)-tolune (SMPT), N-succinimidyl 3-(2-pyridyldithio) propionate (SPDP), succinimidyl 6-[3-(2-pyridyldithio) propionate] hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo.

In addition to the heterobifunctional cross-linkers, there exists a number of other cross-linking agents including homobifunctional and photoreactive cross-linkers. Disuccinimidyl suberate (DSS), bismaleimidohexane (BMH) and dimethylpimelimidate.2 HCl (DMP) are examples of useful homobifunctional cross-linking agents, and bis-[13-(4-azidosalicylamido)ethyl]disulfide (BASED) and N-succinimidyl-6(4-azido-2'-nitrophenyl-amino)hexanoate (SANPAH) are examples of useful photoreactive cross-linkers for use in this invention. For a recent review of protein coupling techniques, see Means et al. (1990) Bioconjugate Chemistry 1:2-12, incorporated by reference herein.

One particularly useful class of heterobifunctional cross-linkers, included above, contain the primary amine reactive group, N-hydroxysuccinimide (NHS), or its water soluble analog N-hydroxysulfosuccinimide (sulfo-NIHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product.

In certain embodiments, the lipophilic moiety employed is a lipid moiety. Generally, a "lipid" is a member of a heterogeneous class of hydrophobic substances characterized by a variable solubility in organic solvents and insolubility, for the most part, in water. The principal class of lipids that are encompassed within this invention are fatty acids and sterols (e.g., cholesterol). Derivatized proteins of the invention contain fatty acids which are cyclic, acyclic (i.e., straight chain), saturated or unsaturated, mono-carboxylic acids. Exemplary saturated fatty acids have the generic formula: $CH_3(CH_2)_nCOOH$. The following table lists examples of some fatty acids that can be derivatived conveniently using conventional chemical methods.

TABLE I

Exemplary Saturated and Unsaturated Fatty Acids.
Saturated Acids: CH3(CH2)n COOH

| Value of n | Common Name |
|---|---|
| 2 | butyric acid |
| 4 | caproic acid |
| 6 | caprylic acid |
| 8 | capric acid |
| 10 | lauric acid |
| 12 | myristic acid |
| 14 | palmitic acid |
| 16 | stearic acid |
| 18 | arachidic acid |
| 20 | behenic acid |
| 22 | lignoceric acid |

Unsaturated Acids

| | |
|---|---|
| CH3CH=CHCOOH | crotonic acid |
| CH3(CH2)3CH=CH(CH2)7COOH | myristoleic acid |
| CH3(CH2)5CH=CH (CH2)7COOH | palmitoleic acid |
| CH3(CH2)7CH=CH(CH2)7COOH | oleic acid |
| CH3(CH2)3(CH2CH=CH)2(CH2)7COOH | linoleic acid |
| CH3(CH2CH=CH)3(CH2)7COOH | linolenic acid |
| CH3(CH2)3(CH2CH=CH)4(CH2)3COOH | arachidonic acid |

Other lipids that can be attached include branched-chain fatty acids and those of the phospholipid group such as the phosphatidylinositols (i.e., phosphatidylinositol 4-monophosphate and phosphatidylinositol 4,5-biphosphate), phosphatidycholine, phosphatidylethanolamine, phosphatidylserine, and isoprenoids such as farnesyl or geranyl groups.

Cell Administration

A variety of means for administering cells to subjects will, in view of this specification, be apparent to those of skill in the art. Such methods include injection or implantation of the cells into a target site in a subject. Cells may be inserted into a delivery device which facilitates introduction by injection or implantation into the subjects. Such delivery devices may include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The cells may be prepared for delivery in a variety of different forms. For example, the cells may be suspended in a solution or gel or e bedded in a support matrix when contained in such a delivery device. Cells may be mixed with a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention may be prepared by incorporating cells as described herein in a pharmaceutically acceptable carrier or diluent and, as required, other ingredients enumerated above, followed by filtered sterilization.

Exemplification

The invention now being generally described, it will be more readily understood by reference to the following examples, which are included merely for purposes of illustration of certain aspects and embodiments of the present invention, and are not intended to limit the invention.

Rabbit Articular Chondrocytes

New Zealand rabbit articular chondrocytes were harvested as previously described (Wakitani et al., 1998, *Tissue Eng.*, 4:429-44.) with minor alterations. Briefly, rabbit distal femoral condyles and proximal humeral condyles were harvested after the rabbits have been sacrificed by Fatal-Plus® (Vortech, Dearborn, Mich.) injection. The articular cartilage layer was scraped off the condyle using a scalpel, minced into 1 $mm^2$ pieces which were digested in a mixture of enzymes (Collagenase 1%, Trypsin 0.05% and Chondroitinase 0.1%) in Dulbecco's modified Eagle's Medium over night at 37° C. in 5% $CO_2$/95% air with constant gentle mixing. The mixture was filtered through a 70 μm filter to obtain a single cell suspension. The filtered solution was centrifuged at 300×g for five minutes and supernatant discarded and replaced with fresh Dulbecco's Modefied Eagle's Medium (DMEM) supplemented with 10% selected lots (Lennon, et al., 1995, *Exp Cell Res.*, 219:211-22) of fetal calf serum (FCS, Gibco BRL, Gaithersburg, Md.) and antibiotic-antimycotic solution (Penicillin G sodium: 100 U/ml, Amphotericin B: 0.5 !g/ml, streptomycin sulfate: 100 μg/ml; Gibco/BRL). The cells were counted with a hemocytometer and plated in 100 mm Petri-dishes at $2.0 \times 10^5$ cells per plate. The first medium change is done 48-72 hours after plating after which the medium is changed twice a week.

Palmitation of Protein G

Recombinant protein G (Sigma, St. Louis, Mo.) was derivatized with N-hydroxysuccinimide ester of palmitic acid (Sigma, St. Louis, Mo.) using the procedure described by Kim and Peacock (Kim, et al., 1993, *J Immunol Methods*, 158:57-65) for palmitation of protein A. The lipid-derivatized protein G was purified on a 10 ml Sephadex G-25 (Pharmacia, Piscataway, N.J.) column equilibrated with PBS containing 0.1% deoxycholate (DOC) pH 7.4. The protein concentration was adjusted to 750 μg/ml by O.D. absorbance (UV-160 spectrophotometer, Shimadru) at 280 nm according to standard curves, 20 μm filter sterilized, and stored at 4° C. until used.

Membrane Incorporation of Palmitated Protein G and the Effects on Cell Viability and Mitotic Potential.

In vitro expanded chondrocytes were trypsinized off the plates, washed three times in serum free DMEM and re-suspended at a density of $3-4 \times 10^6$/ml in DMEM. Varying concentrations of palmitated protein G (PPG) or non-derivatized protein G (as a negative control) were added to the cell suspension, and the mixture was incubated at 37° C. for 2 hours with constant gentle mixing. To assess the incorporation of PPG onto cell surfaces, the cells were washed twice in the buffer (PBS, 0.1% DOC pH 7.4) and then incubated at 4° C. for 1 hour with 100 μl of 100 μg/ml of FITC-human IgG (Sigma) diluted in the same buffer (per $1.0 \times 10^6$ cells). Cells were washed three times in the buffer and analyzed at the Flow Cytometry Core Facility at Case Western Reserve University (National Cancer Institute Core Facility, Cleveland, Ohio, U.S.A.) by fluorescent microscopy. The toxicity of rising concentrations of PPG coating was assessed using pro-pidium iodine uptake as quantified by FACS scan. An aliquot of cells from every concentration was re-plated on 100 mm petri-dishes in complete medium allowed to attach and incu-bated at 37° C. in 5% $CO_2$/95% air. The cells were trypsinized after one week incubation, counted by a hemocytometer to determine the effects of PPG coating on cell growth.

Aggregate Cultures

Aggregate cultures (Yoo et al., 1998, *J Bone Joint Surg Am.*, 80:1745-57) were used to assess chondrogenic potential of antibody-coated cells. Cells were coated with a range of coating concentrations of PPG (0-60 μg/ml) and a second coating with human FITC IgG antibody. Cells were placed in 0.5 ml of defined medium (Dulbecco's Modified Eagle medium base supplemented with 6.25 µg/ml insulin, 6.26 µg/ml transferrin, 6.25 µg/ml selenious acid, 5.35 µg/ml linoleic acid, 1.25 µg/ml bovine serum albumin (BSA), 1 mM pyruvate, and 37.5 ng/ml ascorbate-2-phospate) $2.0 \times 10^5$ cells per 15 ml polypropylene conical tube and centrifuged at 500×g for five minutes. The pellets were incubated at 37° C. in 5% $CO_2$/95% air, for three weeks with medium changes every other day. Within the first 24 hours, the cells formed a free-floating pellet. At three weeks, the pellets were harvested and fixed in 10% neutral buffered formalin for standard histology. The chondrogenic phenotype was assessed by examination of histologic sections stained with toluidine blue (chondrogenic cells are round, surrounded by a meta-chromatic staining representing highly sulfated glycosaminoglycans). In order to further verify the phenotype of the cells within the aggregates, type II collagen immunohistochemistry staining was carried out as previously described (Naumann, et al., 2002, *J Histochem Cytochem.*, 50:1049-58). Briefly, sections were rehydrated with PBS for 5 minutes, and digested with bovine testis Hyalruronidase 8000 U/ml (Sigma H-3506) for 60 minutes. A second digestion was performed using Pronase 1 mg/ml (Sigma P-5147) for 15 minutes at 20° C. after which non-specific adhesion sites were blocked using 3% BSA. Next, the sections were stained with mouse anti-collagen type II IgG (II-116B3) diluted in 3% BSA 1:200 for 60 minutes. The slides are washed with 3% BSA and coated with second layer of horseradish peroxidase-conjugate goat-anti mouse IgG. Slides were washed in PBS and contrasted in a solution of Vector VIP Substrate (Vector labs; Burlin-game, CA) according to the manufacturers instructions, washed and counterstained with fast green. The slides were observed on an Olympus BH-2 fluorescence microscope.

Cell Coating with Matrix Specific Antibodies.

Cells pre-coated with PPG were washed twice in buffer and then incubated at 4° C. for 1 hour with 100 µl of 100 µg/ml cartilage matrix specific antibodies diluted in the same buffer (per $1.0 \times 10^6$ cells). The cartilage matrix specific antibodies used were: mouse anti-chondroitin 4 sulfate IgG (2B6), mouse anti-chondroitin 6 sulfate IgG (3B3; Seikasaku Kogyo, Inc., Tokyo), mouse anti-keratan sulfate IgG (5D4) (Caterson, Iowa City, Iowa). After this initial incubation the cells were washed twice in the same buffer and incubated for 1 hour with FITC-conjugated F(ab)'2 goat anti-mouse antibody (Sigma) diluted in the same buffer. After this last incubation the cells were washed and the efficiency of coating was assessed by FACS.

Vybrant™ Staining of Cells

One day prior to coating of the cells with PPG, the cells were incubated in 10 µM Vybrant™ (Molecular Probes, Eugene, Oreg.) in Hank's balanced salt solution for 15 minutes at 37° C. in 5% $CO_2$/95% air after which they were washed once with Hank's balanced salt solution and fresh medium was added. This vital staining of cells is based on the passive diffusion of a colorless, nonfluorescent carboxy-fluorescein diacetate succinimidyl ester (CFDA SE) into cells. Once in the cell, the CFDA SE is cleaved by intracellular esterases to yield a highly fluorescent dye which is retained in some cells for a number of weeks. Staining of the cells was verified by fluorescent microscopy after trypsinization of the cells and before the PPG coating procedure.

Frozen Sections 5-8 µm frozen sections of rabbit articular cartilage were cut and placed onto 3-amino propyltriethoxysilane coated slides (Sigma) and stored at −20° C. until use. When tested the slides were first hydrated in PBS for 30 minutes. Half the sections were incubated in chondroitinase ABC (0.1 U/ml) for 15 minutes, and all sections were then blocked with 1% BSA/PBS for 5 minutes. Next, the sections were incubated for 45 minutes with 30 µl of $10 \times 10^6$ Vybrant™ stained cells in PBS coated with different antibodies (or PPG as a negative control). After the incubation time the sections are gently and meticulously washed with PBS for 5 minutes, suspended for 30 seconds in 5 µg/ml propidium iodine, washed again, and cover-slipped with 1 mg/ml p-phenylendiamine in 45% glycerol in 1 N sodium phosphate, pH 8.5. The slides were analyzed using fluorescent microscopy.

Osteo-Chondral explants

Osteo-Chondral explants were harvested from 1-year-old male New Zealand white rabbits after they were sacrificed by intra-venous phenobarbital overdose (2,600 mg/kg; Fetal-Plus, Vortex Pharmaceuticals, Dearborn, Mich.). The distal femoral condyles were sterilely harvested and 4.25 mm diameter trephine is used to manually harvest 3-4 osteo-chondral cylinders from every femur. A standard defect is then created by sliding a 1 mm diameter ring curette along the cartilage surface, this is performed taking care as to not penetrate the subchondral bone. These explants were incubated in a 96-well plate with the cartilage side facing up and the different Vybrant™ stained cells ($1.5 \times 10^6$ cells/well) coated with the different antibodies are applied to the well on top of the explants and incubated for 45 minutes at 37° C. in 5% $CO_2$/95% air. Following this incubation, the explants were turned cartilage side facing down into empty wells filled with DMEM. Using a conical insert, the cartilage is kept above the bottom of the well thus allowing gravity to affect the attached cells. This incubation was carried out for 12 hours. The explants are then harvested, fixed in 10% neutral buffered formalin, decalcified, embedded, and analyzed by fluorescent microscopy.

Membrane Incorporation of Palmitated Protein G and the Effects on Cell Viability and Mitotic Potential A two-step strategy was developed for quantitatively coating cells with cartilage matrix specific antibodies. The first set of optimization procedures is aimed at efficiently coating cells with PPG. In order to coat cells with antibodies from different species, it was necessary to test the use of PPG in the coating procedure. To test the ability of PPG to coat cells, cells were incubated in a range of PPG concentrations and as a negative control, cells incubated with buffer only or with non-palmitated protein G. Cells incubated with buffer only or with non-palmitated protein G did not bind significant amounts of FITC labeled human IgG (FIG. 1). A linear increase of mean fluorescence intensity was observed in samples incubated in 10-60 µg/ml of PPG (FIG. 1). To verify coating of the cells with the second layer of matrix specific antibodies (2B6, 3B3, 5D4 and II-116B3), cells incubated in primary antibodies were washed and incubated with goat anti-mouse FITC labeled antibody (F(ab')$_2$ fragment). After washing the cells twice in buffer, fluorescence was quantified by FACS (results not shown). The results showed that PPG coated cells were, in fact, coated with matrix specific antibodies.

Effects of Coating with PPG on Cell Viability, Mitotic Potential and Chondrogenic Phenotype.

Figure 2:
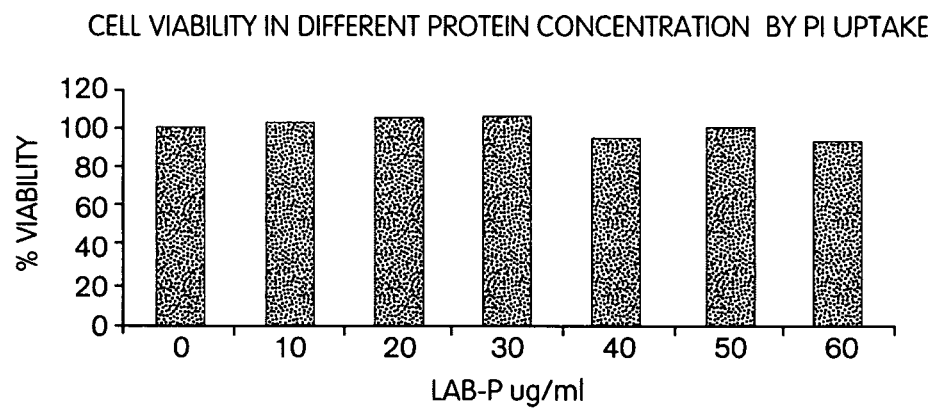
FIG. 2. Cell viability is indicated as a percentage of the starting cell number prior to treating with LAB-P(PPG). No significant loss of cell numbers were observed at any concentration of LAB-P that was used.

Propidium iodine uptake, assessed by FACS, was used to assess the effects of the coating procedure on cellular viability. The results (FIG. 2) showed above 95% viability of cells coated with concentrations of up to 60 µg/ml PPG.

Figure 3:
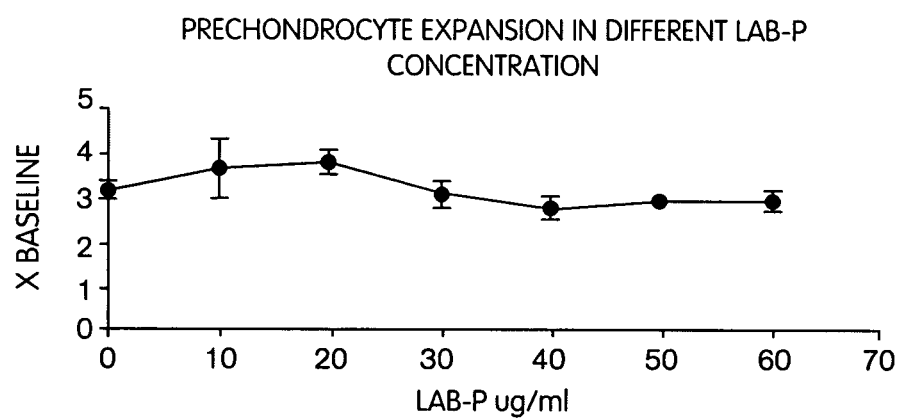
FIG. 3. Cells coated with different concentrations of LAB-P were cultured for one week in standard culture medium and were shown to expand approximately 3 fold at all coating concentrations tested.

Mitotic expansion of PPG cells was analyzed by incubating identical number of cells ($2.0 \times 10^5$) coated with different concentration of PPG in 100 mm petri-dishes. After 1 week of incubation at 37° C. in 5% $CO_2$/95% air the cells were trypsinized and counted. These results showed no adverse effect of cell painting on mitotic expansion. PPG coated cells tripled in number in all PPG concentrations tested (10-60 µg/ml) and no significant differences were observed between PPG samples and uncoated controls (FIG. 3).

Figure 4:
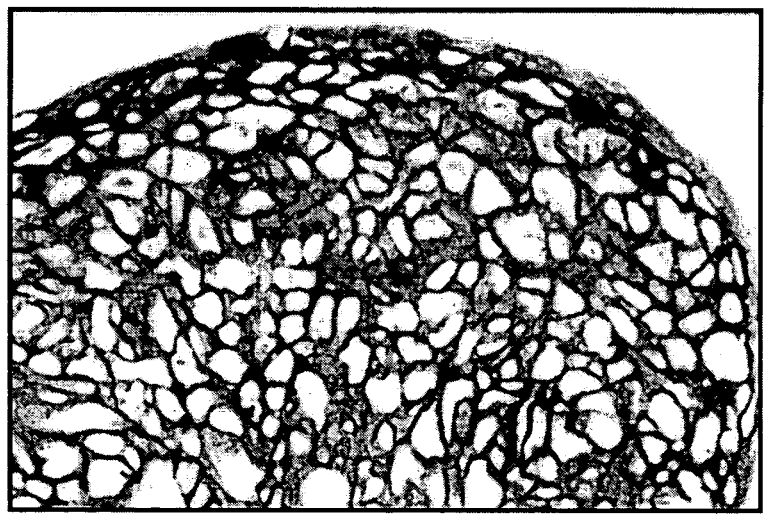
FIG. 4. Pre-chondrocytes coated with 60 μg/ml of PPG were cultured in chondrogenic conditions for 3 weeks, harvested, fixed, embedded, sectioned and then stained for collagen type II. The intense purple staining indicates the presence of type II collagen indicating that the coating procedure has not interfered with the ability of these cells to differentiate into chondrocytes. The sample was counter-stained with Fast Green.

Cells coated with PPG-FITC labeled human IgG formed oval aggregates after 1 week in culture in chondrogenic culture conditions, and generally grew in size by 3 weeks in culture. Histologic examination of toluidine blue-stained 5-µm sections of three week old aggregates showed rounded cells surrounded by abundant meta-chromatic stained matrix indicating a high sulfated glycosaminoglycan content (FIG. 4), which correlates with cartilage matrix. To confirm the chondrocyte phenotype in these samples, sections were assayed by immunohistochemistry for expression of collagen type II, and this analysis revealed the presence of collagen type II plus cell matrix (data not shown).

Targeting Frozen Sections

Figure 5:
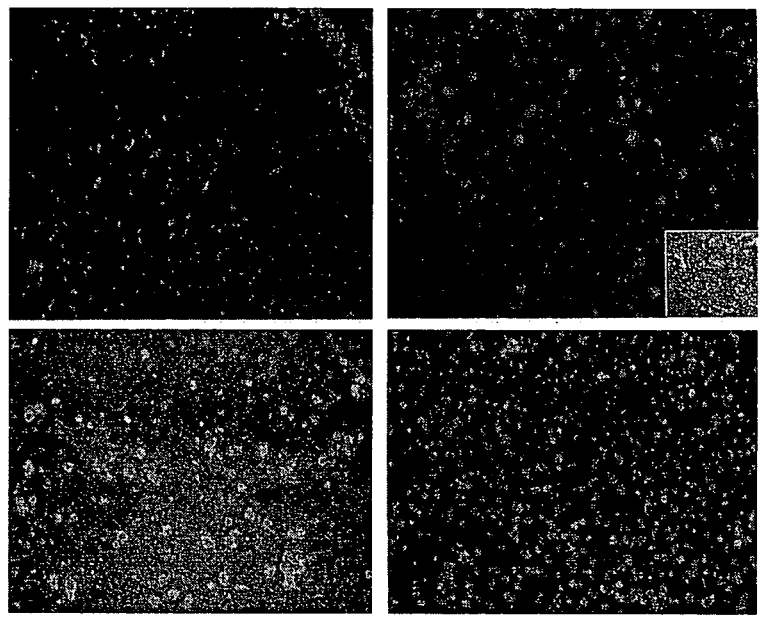
FIG. 5. Targeting of Vybrant™-stained cells to frozen sections of cartilage. Vybrant™ cells (green) are shown on the surface of the rabbit articular cartilage sections; cartilage nuclei are stained red with propidium iodide. Upper left shows control cells (PPG only); only a few cells adhere. Upper right shows cells coated with PPG+anti-type II collagen antibody. Lower left shows PPG+anti-chondroitin-4-sulfate. Lower right shows PPG+anti-keratan sulfate. Each of the three samples incubated with cells containing the targeting antibody had more Vybrant™positive cells than did control.

The chondrocytes were first incubated in a vital dye, Vybrant™, which is metabolized into the fluorescent molecule only by living cells. Once the cells were stained they were coated with PPG and a second layer of matrix specific antibodies. Fluorescent micrographs showed that cells coated with specific matrix antibodies are found in greater density on the sections than in controls (FIG. 5).

Osteo-Chondral Explants

Figure 6:
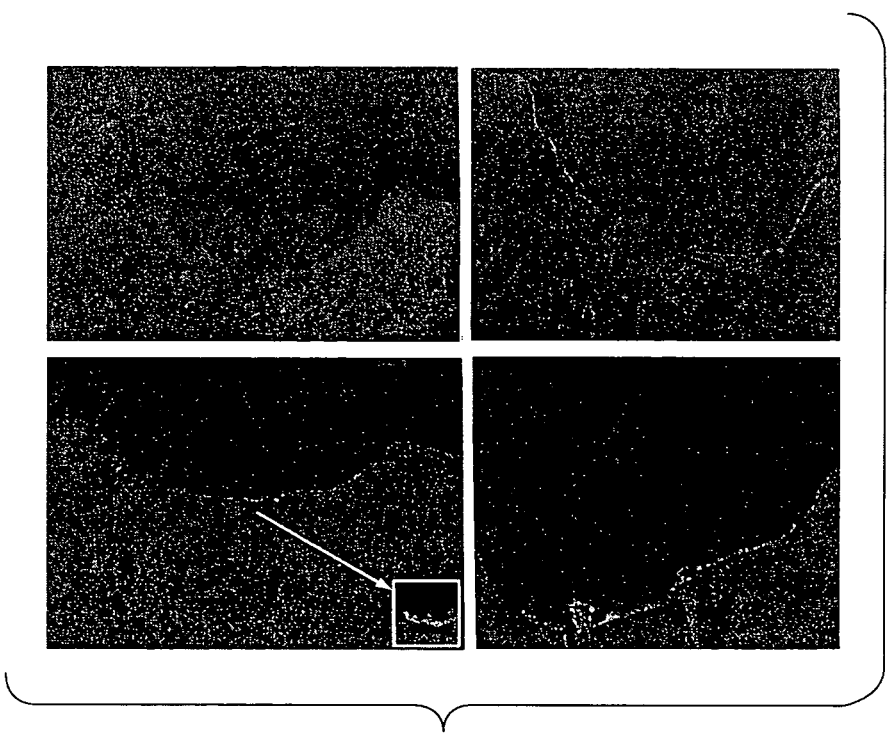
FIG. 6. Explants of rabbit articular cartilage incubated with Vybrant™-stained cells. Upper left shows cells coated with PPG only. Only one cell is visible on the left side of the u-shaped defect. Upper right is chondoroitin-4-sulfate antibody. Lower left is collagen II (arrow points to insert showing a higher magnification of Vybrant™-positive cells). Lower right is both antibodies in combination. Each of the antibody coated cell preparations showed greater numbers of positive cells in the PPG only control.
Figure 7A:
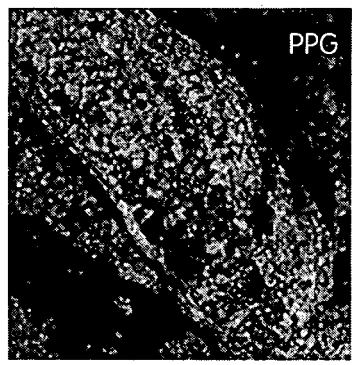
FIG. 7. Confocal imaging of targeted cartilage explants. Fluorescently-labeled cells (incubated in 10 μM Vybrant™) with and without pre-coating with antibodies were incubated with cartilage explants, washed in buffer, fixed and then observed and analyzed by confocal microscopy. Optical slices were collected at 30 μm intervals from the bottom of the defect to the articular surface and the images were processed by Z-stacking using Zeiss LSM software. Control cells coated with PPG only (A) showed nearly no affinity for undamaged cartilage surfaces while the defect area had a low fluorescent signal. Cells coated with an antibody to type II collagen (B) generally showed a moderate increase in fluorescent signal compared to PPG only. Cells coated with two antibodies (C) such as anti-type II collagen and anti-chodroitin-4-sulfate (2B6) showed a much greater intensity of fluorescence than PPG only samples, as did coating with triple antibodies (D) to type II collagen, chondroitin-4-sulfate and keratan sulfate (5D4).
Figure 7B:
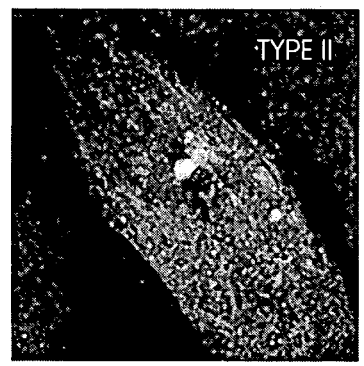
Figure 7C:
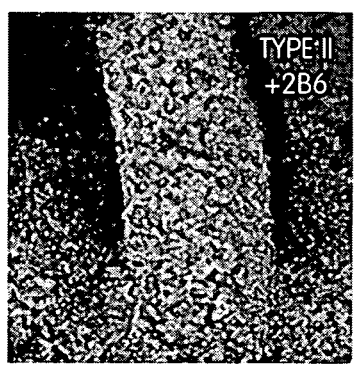
Figure 7D:
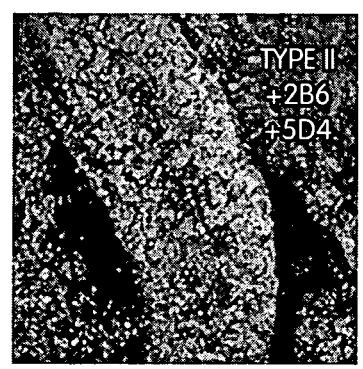
Figure 8:
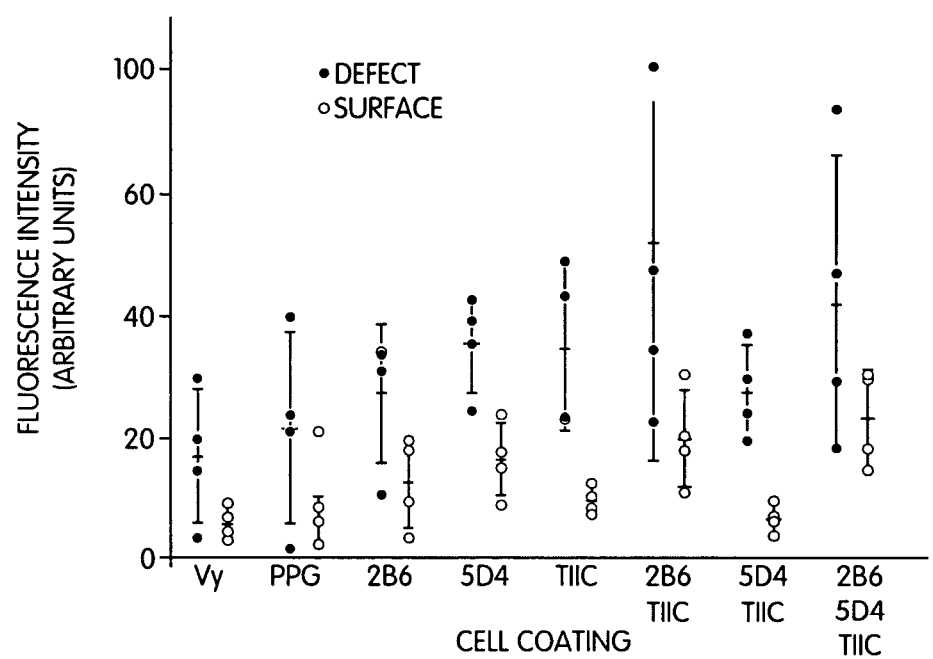
FIG. 8. Quantification of confocal microscopic fluorescent signal in rabbit cartilage explants. Fluorescent microscopic images were collected throughout the depth of the cartilage defect and Z-stack images formed with Zeiss LSM software. The intensity of the Z-stacked images was analyzed with Metamorph software and the intensities with the defect area (dark circles) and the cartilage surface (open circles) was determined for 4 separate samples. The fluorescent signal within the defect was always greater than that detected on the undamaged cartilage surface in all samples. There was a trend of increasing fluorescent signal in single antibody coated samples, but only samples coated with antibodies to both chondroitin-4-sulfate (2B6) and collagen II (TIIC) or triple-coated with 2B6, TIIC and antibody to keratan sulfate (5D4) showed a significant increase in intensity compared to controls at $p<0.05$ (ANOVA).

To test the ability of antibody-coated cells to preferentially bind to cartilage matrix, Vybrant™ labeled cells were used in order to assess the targeting potential of our antibody coated cells. A system was developed to allow us to create a standard articular defect in an osteochondral explant. Fluorescent micrograph revealed greater number of cells preferentially inside the defect than on the native cartilage surface when specific antibodies were used and a different morphology of the cells inside the defect. Cells that adhered inside the defect without specific antibody coating had a flattened appearance while specifically targeted cells seem to be round and clumped in groups. It also appears that combining the different antibodies together in the coating of cells has an additive effect (FIGS. 6, 7 and 8).

Incorporation by Reference

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed:

1. A composition for targeting a chondrogenic cell to a cartilage matrix comprising:
   a chondrogenic cell; and
   a targeting moiety that binds to an epitope of cartilage matrix, said targeting moiety being selected from the group consisting of an antibody and an antibody fragment;
   wherein said chondrogenic cell is linked to said targeting moiety, and
   wherein the linked targeting moiety enhances adherence of the chondrogenic cell to cartilage matrix when administered to a cartilage matrix injury site and wherein the linked targeting moiety does not adversely affect chondrogenic cell viability, mitotic potential, and phenotype.

2. The composition of claim 1, wherein said antibody is a monoclonal antibody.

3. The composition of claim 1, wherein said antibody is a polyclonal antibody.

4. The composition of claim 1, wherein said antibody is selected from the group consisting of anti-collagen type II, anti-chondroitin 4-sulfate and anti-keratan sulfate.

5. The composition of claim 1, wherein said antibody is modified with a hydrophobic moiety.

6. The composition of claim 5, wherein said hydrophobic moiety is a palmitoyl moiety.

7. The composition of claim 5, wherein said hydrophobic moiety is a myristoyl moiety.

8. The composition of claim 1, wherein said antibody fragment is selected from the group consisting of Fv fragment, single chain Fv (scFv) fragment, Fab' fragment, F(ab')2 fragment, single domain antibody, camelized antibody, humanized antibody, diabodies, tribodies, and tetrabodies.

9. The composition of claim 1, wherein said chondrogenic cell is linked to said targeting moiety directly.

10. The composition of claim 1, wherein said chondrogenic cell is linked to said targeting moiety via a linker.

11. The composition of claim 10, wherein said linker is selected from the group consisting of protein G and protein A.

12. A composition for targeting a chondrogenic cell to a cartilage matrix comprising:
    a chondrogenic cell; and
    an antibody that binds to an of epitope of cartilage matrix, the antibody being selected from the group consisting of anti-collagen type II antibodies, anti-chondroitin 4-sulfate antibodies, and anti-keratan sulfate antibodies;
    wherein said chondrogenic cell is linked to said antibody by a palmitoyl moiety, and wherein the linked antibody enhances adherence of the chondrogenic cell to cartilage matrix when administered to a cartilage matrix injury site and does not adversely affect chondrogenic cell viability, mitotic potential, and chondrogenic phenotype.

13. The composition of claim 12, wherein said antibody is a monoclonal antibody.

14. The composition of claim 12, wherein said antibody is a polyclonal antibody.

15. The composition of claim 12, wherein said antibody is selected from the group consisting of Fv fragment, single chain Fv (scFv) fragment, Fab' fragment, F(ab')2 fragment, single domain antibody, camelized antibody, humanized antibody, diabodies, tribodies, and tetrabodies.

16. A composition for targeting a chondrogenic cell to a cartilage matrix comprising:
    a chondrogenic cell;
    a first antibody that binds to an epitope of cartilage matrix, the first antibody comprising an anti-collagen type II antibody;
    a second antibody that binds to an epitope of cartilage matrix, the second antibody comprising an anti-chondroitin 4-sulfate antibody;
    wherein said chondrogenic cell is linked to the antibodies by a palmitoyl moiety, and wherein the linked antibodies enhance adherence of the chondrogenic cell to cartilage matrix when administered to a cartilage matrix injury site and do not adversely affect chondrogenic cell viability, mitotic potential, and chondrogenic phenotype.

17. A composition for targeting a chondrogenic cell to a cartilage matrix comprising:
- a chondrogenic cell;
- a first antibody that binds to an epitope of cartilage matrix, the first antibody comprising an anti-collagen type II antibody;
- a second antibody that binds to an epitope of cartilage matrix, the second antibody comprising an anti-chondroitin 4-sulfate antibody; and
- a third antibody that binds to an epitope of cartilage matrix, the third antibody comprising an anti-keratan sulfate antibody;
- wherein said chondrogenic cell is linked to the antibodies by a palmitoyl moiety, and wherein the linked antibodies enhance adherence of the chondrogenic cell to cartilage matrix when administered to a cartilage matrix injury site and do not adversely affect chondrogenic cell viability, mitotic potential, and chondrogenic phenotype.

\* \* \* \* \*